US008200317B2

(12) United States Patent
Baxi et al.

(10) Patent No.: US 8,200,317 B2
(45) Date of Patent: Jun. 12, 2012

(54) METHOD AND APPARATUS FOR AMPLIFYING MULTIPLE SIGNALS USING A SINGLE MULTIPLEXED AMPLIFIER CHANNEL WITH SOFTWARE CONTROLLED AC RESPONSE

(75) Inventors: Amit S. Baxi, Maharashtra (IN); RamKumar Peramachanahalli, Karnataka (IN)

(73) Assignee: Intel Corporation, Santa Clara, CA (US)

( * ) Notice: Subject to any disclaimer, the term of this patent is extended or adjusted under 35 U.S.C. 154(b) by 1167 days.

(21) Appl. No.: 11/478,530

(22) Filed: Jun. 30, 2006

(65) Prior Publication Data

US 2008/0004536 A1 Jan. 3, 2008

(51) Int. Cl.
*A61B 5/04* (2006.01)
(52) U.S. Cl. ........................................ 600/509; 600/508
(58) Field of Classification Search .................. 600/508, 600/509
See application file for complete search history.

(56) References Cited

U.S. PATENT DOCUMENTS

| 5,205,294 | A | * | 4/1993 | Flach et al. | 600/508 |
| 5,694,943 | A | | 12/1997 | Brewer et al. | |
| 6,238,338 | B1 | * | 5/2001 | DeLuca et al. | 600/300 |
| 6,366,803 | B1 | * | 4/2002 | Fee | 600/509 |
| 6,486,635 | B1 | * | 11/2002 | Matsuda et al. | 320/134 |
| 2007/0231642 | A1 | * | 10/2007 | Stengelin et al. | 429/23 |
| 2008/0027338 | A1 | * | 1/2008 | Lu et al. | 600/509 |

FOREIGN PATENT DOCUMENTS

| EP | 1611845 | 1/2006 |
| JP | 08-504344 T | 5/1996 |
| JP | 11-002671 A | 1/1999 |
| JP | 2003-174340 A | 6/2003 |
| JP | 2005-503883 T | 2/2005 |
| JP | 2005-210261 A | 8/2005 |
| JP | 2002-529118 T | 12/2010 |
| WO | 94/13197 | 6/1994 |

OTHER PUBLICATIONS

Japanese Office Action with English translation corresponding to Japanese Patent Application No. 2009-510204, dated Oct. 12, 2010.
Japanese Office Action with English translation corresponding to Japanese Application No. 2009-510204, dated Jul. 26, 2011, 6 pages.

* cited by examiner

*Primary Examiner* — Carl H Layno
*Assistant Examiner* — Jennifer Ghand
(74) *Attorney, Agent, or Firm* — Pillsbury Winthrop Shaw Pittman LLP (57) ABSTRACT

A device for amplifying multiple signals includes a plurality of sensors, where a plurality of lead signals are derived from the plurality of sensors, a plurality of low-pass filter and buffer amplifiers for filtering and buffering the plurality of lead signals, one or more multiplexers, where outputs from the plurality of low-pass filter and buffer amplifiers are input to one of the one or more multiplexers, a single amplifier channel, where the outputs of the one or more multiplexers are input to the single amplifier channel and a microcontroller which controls the one or more multiplexers, wherein the microcontroller stores software which selects, in sequence, one at a time, one out of each of the lead signals to be connected to inputs of the single amplifier channel, wherein the single amplifier channel amplifies all of the lead signals. The single amplifier channel has a software programmable AC response.

13 Claims, 5 Drawing Sheets

METHOD AND APPARATUS FOR AMPLIFYING MULTIPLE SIGNALS USING A SINGLE MULTIPLEXED AMPLIFIER CHANNEL WITH SOFTWARE CONTROLLED AC RESPONSE

FIELD OF INVENTION

The embodiments of the invention relate to methods and apparatus for multiplexing a single analog amplifier channel to amplify multiple signals while controlling the amplifier's alternating current AC response through software.

BACKGROUND

A number of biomedical devices such as Electrocardiography (ECG), Electroencephalography (EEG), Electromyography (EMG), etc. require amplification of a number of bio-signals sensed from a number of electrodes attached to a patient. Usually, such equipment uses repeated stages of identical analog amplifier circuitry to amplify each of the signals sensed by the electrodes. This results in increased hardware, power consumption, form factor and cost. For example, a typical 12-Lead ECG system requires eight identical analog amplifier channels for amplifying signals from a combination of 10 electrodes attached to a patient. The remaining four ECG signals are computed mathematically from the eight amplified signals. Each ECG amplifier channel is implemented with a number of analog components.

Usually, such amplifiers need a band pass frequency response from near direct current DC to several hundred hertz. For example, a diagnostic ECG amplifier requires a frequency response from 0.05 Hz to 150 Hz. In order to get 0.05 Hz high-pass frequency response, it is necessary to use AC coupled amplifier stages with large time constants, which have long settling times (in several seconds). Since the settling time of the AC coupled (high-pass filter (HPF)) stage of such an amplifier channel is quite high, it is not possible to multiplex a single analog amplifier channel to amplify multiple signals.

In the conventional ECG, each of the eight ECG channels is implemented with individual differential amplifiers, high-pass filters, gain amplifiers and anti-aliasing filters. If N equals the number of identical amplifier channels (N=8 in case of 12-Lead ECG), C equals the number of electronic components per channel and F equals the components required for the RL-drive circuit and input buffers, then the total number of electronic components needed to implement a conventional 12-Lead amplifier system equals (N×C)+F. The total number of components in identical amplifier channels, taken together, is much higher than the components in RL drive and input buffers. Hence, N×C>>F. Increased numbers of components increases the printed circuit board complexity, the cost, the form factor and results in higher power consumption.

Further, in the conventional ECG, aging of analog components and environmental factors such as temperature variation can cause drifts and artifacts in the measured signals. Since each ECG channel is physically separate, each ECG channel is subject to a different drift due to environmental and component variations.

DETAILED DESCRIPTION

In the following detailed description, a 12-Lead ECG Single Multiplexed Amplifier Channel application is presented to demonstrate the working and effectiveness of embodiments of the invention and should not be taken in a limiting sense. The signal amplification technique described herein can be used to amplify a variety of analog signals in different applications such as in Pulse Oximetry, Non-Invasive Blood Pressure measurement, Electromyography (EMG), Electroencephalography (EEG) etc., which require amplification of low voltage, low frequency signals riding on static as well as time varying DC offsets. This signal amplification technique can also be extended to other industrial and control applications which need to amplify signals from a variety of sensors.

A 12-Lead ECG system requires amplifying at least eight different ECG lead signals, which are sensed by a combination of 10 electrodes attached to a patient. ECG signals are of the order of about 1 mV and riding on DC offsets anywhere between 0 to 250 mV. The DC offsets are different for different electrode combinations. Moreover, these DC offset voltages are also subject to drift, which may result in a drift of the ECG signal's baseline.

In order to amplify a 1 mV ECG, to say 1V, it is necessary to remove the much higher DC potentials (which are not of interest) from the ECG signal so that the gain amplifiers do not go into saturation.

The required amplifier frequency response for diagnostic-quality ECG is from 0.05 Hz to 150 Hz, and for monitoring-quality ECG, the required amplifier frequency response is from 0.5 Hz to 40 Hz.

In order to get a 0.05 Hz or 0.5 Hz high-pass frequency response, it is necessary to use AC coupled amplifier stages with large time constants and long settling times (in several seconds). Since the settling time of the AC coupled (high-pass filter (HPF)) stage of such an amplifier channel is quite high, it is not possible to multiplex a single analog amplifier channel to amplify multiple signals.

The embodiments of the invention described herein are capable of amplifying multiple signals using a single multiplexed amplifier channel with software controlled AC response and addressing the problems related to multiplexing AC coupled amplifiers with long settling times. The embodiments of the invention may reduce the number of hardware components, power consumption, form factor, cost and also provide additional benefits like software programmable AC response, enhanced features and improved stability.

According to an embodiment of the invention, an apparatus for amplifying multiple lead signals includes multiplexers, wherein the lead signals are input to the multiplexers, a single amplifier channel, where the outputs of the multiplexers are input to the single amplifier channel, and a microcontroller which controls the multiplexers, wherein the microcontroller stores software which selects, in sequence, one at a time, one out of each of the lead signals to be connected to inputs of the single amplifier channel, wherein the single amplifier channel amplifies all of the lead signals.

According to this embodiment, the single analog amplifier channel may include a differential amplifier, a programmable gain amplifier and an anti-aliasing filter. The analog-to-digital converter and a digital-to-analog converter may be external to the microcontroller or may be included inside the microcontroller. A selected lead signal may be connected to an input of the differential amplifier and the output of the differential amplifier may be fed to an input of the programmable gain amplifier for DC offset removal and further amplification. The output of the programmable gain amplifier may be filtered by the anti-aliasing filter and the output of the anti-aliasing filter may be digitized by the analog-to-digital converter of the microcontroller. The microcontroller may then select a next lead signal to be amplified by using the analog multiplexers.

According to an embodiment of the invention, the microcontroller may store software which simulates a high-pass filter to remove DC offset by computing the DC offset from a voltage signal of each digitized lead, converting the DC offset to an analog representation by the digital-to-analog converter, and subtracting the DC offset back from the same lead signal in a next amplification cycle. The software models a low-pass filter stage for each of the lead signals. According to an embodiment, each low-pass filter computes and tracks the time varying DC offset present in each digitized lead signal. If an output of the low-pass digital filter of a particular lead saturates, a quick baseline restoration algorithm brings the low-pass digital filter and the programmable gain amplifier out of saturation. The frequency response of each of the low-pass digital filters can be changed to a desired value by changing coefficients of the filters in the software, wherein the AC frequency response is programmable in the software.

According to a further embodiment, a maximum gain of the programmable gain amplifier is limited by a ratio of resolution of the digital-to-analog converter to the resolution of the analog-to-digital converter to prevent signal distortion while removing the DC offset. According to yet a further embodiment, the AC response of the single channel amplifier is controlled and changed through software.

According to a further embodiment of the invention, a method of amplifying multiple signals is provided. The method includes deriving a plurality of lead signals by performing differential voltage measurements across a combination of electrodes, selecting, in sequence, one at a time, each of the lead signals to be connected to inputs of a single amplifier channel, time-slicing the single amplifier channel, in a cyclic sequence, between all lead signals, computing a DC drift for each of the sampled lead signals, subtracting the DC drift from each of the respective sampled lead signals in a next sample of the respective lead signals. According to this embodiment, the single amplifier channel amplifies all of the lead signals.

Figure 1:
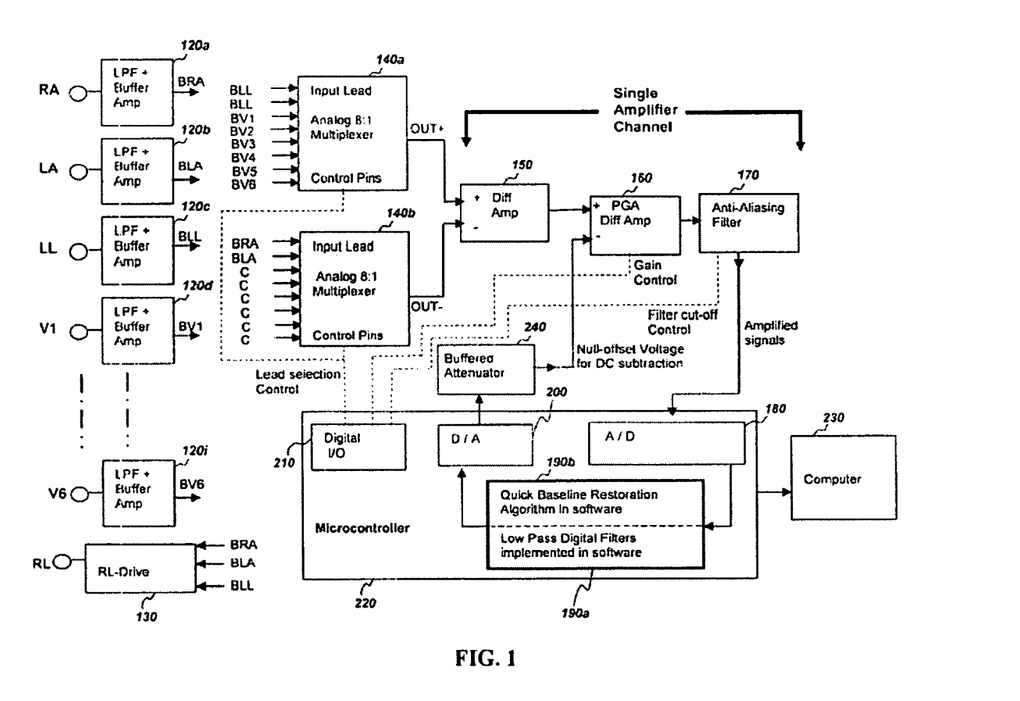
FIG. 1 shows a single multiplexed 12-Lead ECG amplifier according to an embodiment of the invention.

FIG. 1 shows a 12-lead ECG amplifier system designed according to an embodiment of the invention.

Ten ECG electrodes are connected to a patient's body for measuring 12-Lead ECG. Depending on positions where they are connected on the patient's body, the electrodes are designated as RA (Right Arm), LA (Left Arm), LL (Left Leg), RL (Right Leg) and V1 through V6 (electrodes connected to various positions on the chest). These electrodes are connected to the amplifier circuitry using ten wires.

An ECG 'lead' is derived by differential voltage measurements across a combination of the above electrodes. For example, differential voltage across BLL (buffered signal from Left Leg electrode) and BRA (buffered signal from Right Arm electrode), measured at the differential amplifier 150, is used to derive ECG Lead 2 (L2) signal. Similarly, other ECG lead signals are derived by differential measurements.

Typical 12-Lead ECG system needs analog amplification of eight ECG leads and the remaining four ECG leads are mathematically computed from the eight amplified ECG lead signals. Referring to FIG. 1, the typical eight ECG lead combinations, which need analog amplification, are as follows:

$ECG\ Lead2=L2=BLL-BRA$ $ECG\ Lead\ 3=L3=BLL-BLA$ $ECG\ Lead\ V1=V1=BV1-C$, where $C=(BRA+BLA+BLL)/3$ and BV1 through BV6 are buffered signals from the chest electrodes.

$ECG\ Lead\ V2=V2=BV2-C$ $ECG\ Lead\ V3=V3=BV3-C$ $ECG\ Lead\ V4=V4=BV4-C$ $ECG\ Lead\ V5=V5=BV5-C$ $ECG\ Lead\ V6=V6=BV6-C$ The average of signals from RA, RL and LL electrodes is evaluated with inverting summing amplifiers (not shown) at the RL-Drive circuit 130 and fed back to the Right Leg electrode reference potential to reduce common mode noise.

The ECG signals are filtered and buffered by analog low-pass filter and buffer amplifiers 120a through 120i to prevent high frequencies from entering the amplifier stages. The outputs of low-pass filter and buffer amplifiers 120a through 120i are connected to the inputs of two 8-to-1 analog multiplexers 140a and 140b, to enable selection of the required ECG lead. The control pins of these analog multiplexers 140a and 140b are controlled by the digital input/output pins (DIO) 210 of the microcontroller 220.

The microcontroller software selects in sequence, one at a time, one out of eight ECG lead combinations to be connected to the positive and negative inputs of a single analog amplifier channel formed by the differential amplifier 150, the programmable gain amplifier (PGA) 160 and the anti-aliasing filter 170.

As mentioned above, an ECG lead is derived by amplifying the differential voltage across a combination of two or more electrodes using the differential amplifier stage. According to an embodiment of the invention, a single analog amplifier hardware channel is used to amplify all of the required eight ECG lead signals. In order to amplify all the eight ECG lead signals, the microcontroller switches (i.e. time-slices) the amplifier channel between all eight ECG leads, in a cyclic sequence, typically at the rate of 500 times per second per lead for diagnostic-quality ECG.

In each Amplification Cycle, the microcontroller selects the ECG lead to be amplified by controlling the analog multiplexers 140a and 140b using its digital input/output pins (DIO) 210. The selected ECG lead combination is connected to the input of the differential amplifier 150. The output of differential amplifier 150 is fed to the input of programmable gain amplifier (PGA) 160 for DC offset removal and further amplification. The output of programmable gain amplifier 160 is filtered by anti-aliasing filter 170 and then digitized by the analog-to-digital converter (A/D) 180. The microcontroller then selects the next ECG lead signal to be amplified using the analog multiplexers 140a and 140b, and similarly amplifies and digitizes that lead signal. In each Amplification Cycle, all eight ECG lead combinations are selected by the microcontroller 220 in a cyclic sequence (one ECG lead at a time), connected to the inputs of the differential amplifier 150, amplified after DC-removal and then digitized. The digital-to-analog converter (D/A) 200 and the analog-to-digital converter 180 may be either internal or external to the microcontroller.

The Amplification Cycle repeats continuously at a rate of 500 cycles per second for diagnostic-quality ECG, for example. As a result, the single amplifier channel is switched at a rate of (eight ECG lead signals×500 cycles=) 4000 times a second.

The operational amplifiers and associated component values are so chosen that the typical settling time of the analog amplifier channel is much less than 200 microseconds, which is sufficient for such a switching rate.

In order to achieve a very low frequency response (0.05 Hz), an AC coupling stage (high-pass filter for DC removal) with a time constant and settling time of several seconds is required in the conventional ECG analog amplifier channel.

To avoid long settling times in hardware (which would render the fast multiplexing of a single amplifier channel ineffective), the hardware DC removal stage (high-pass filter) is simulated, according to an embodiment of the invention, through software implementation inside the microcontroller's program memory.

According to an embodiment of the invention, the analog AC coupling hardware stage (also known as high-pass filter stage) in the multiplexed amplifier channel is simulated digitally with the help of the low-pass digital filter (LPDF) 190a stages (one LPDF for each ECG lead to be amplified) in the microcontroller's 220 software, a digital-to-analog converter (D/A) 200 and a programmable gain amplifier (PGA) 160.

Continuous DC offset tracking and removal is preferably done by computing the DC offset voltage from the signal of each digitized ECG lead, converting it into an analog representation by the digital-to-analog converter 200, and subtracting it back from the signal of the same ECG lead, in its next Amplification Cycle.

The single amplifier channel is designed in the hardware as a DC amplifier, the DC offset computation and tracking is done by the low-pass digital filters (LPDF) 190a and DC subtraction from the signal is done at the programmable gain amplifier 160.

As stated above, according to an embodiment of the invention, the microcontroller software has eight independent stages of low-pass digital filters (LPDF) 190a implemented in software, one for each ECG lead signal to be amplified. One software implementation of low-pass digital filter is required per ECG lead to be amplified. The low-pass digital filters' cut-off frequency can be changed by changing the filters' coefficient values in software. The output of each respective low-pass digital filter (LPDF) 190a is the time varying DC offset (i.e. DC drift) which is computationally extracted from the ECG signal. According to other embodiments of the invention, it is possible to have different implementations of algorithms in lieu of low-pass digital filters, such as moving average filters, weighted average filters etc., while still performing the same function of DC offset computation.

According to an embodiment of the invention shown in FIG. 1, the microcontroller 220 passes the digital representations of individual ECG lead signals through their corresponding low-pass digital filter software routines 190a to compute and track the DC offsets present in the respective ECG lead signals and stores the digital value of DC offset present in each ECG signal in its memory.

Each Amplification Cycle consists of DC correcting and amplifying all the eight ECG lead signals, one after the other, in a sequence. The microcontroller's timer is configured at the start of the program to trigger a new Amplification Cycle at periodic intervals equal to the inverse of the required sampling rate per ECG lead. For example, for diagnostic-quality ECG, which requires a sampling rate of 500 samples per second per ECG lead, the duration between periodic Amplification Cycles is programmed to be equal to $\frac{1}{500}$ second=2 milliseconds.

Referring to FIG. 1, in each Amplification Cycle, the microcontroller 220 first selects the (one out of eight) ECG lead to be amplified by configuring the control pins of analog multiplexers 140a and 140b using its digital input/output pins (DIO) 210. Then, the microcontroller 220 feeds the digital value of the DC offset, computed for the selected ECG lead in its previous Amplification Cycle, to the digital-to-analog converter (D/A) 200 and generates an equivalent analog voltage called a Null-Offset voltage. This Null-Offset voltage is subtracted from the selected ECG lead signal at the programmable gain amplifier (PGA) 160 to nullify the DC offset, if any, in the ECG signal. The output of programmable gain amplifier 160 is a DC-subtracted and amplified ECG signal, for the selected ECG lead.

The output of the programmable gain amplifier 160, filtered by the anti-aliasing filter 170 is digitized by the microcontroller using the analog-to-digital converter (A/D) 180 and converted to a digital representation. The microcontroller sends the digital representation of the selected ECG lead signal to the computer and also feeds it to the input of the selected ECG lead's low-pass digital filter (LPDF) 190a for DC offset computation and tracking. The output of low-pass digital filter 190a gives a new digital value for the computed DC offset. This newly computed digital value of DC offset is stored in memory to be used for subtraction from the ECG lead signal, in the next Amplification Cycle of the same ECG lead. Once the above DC removal and amplification process is completed for one ECG lead, the microcontroller 220 selects the next ECG lead to be amplified using analog multiplexers 140a and 140b, and repeats the above process for that ECG lead. Similarly, the microcontroller repeats the above amplification process for all the eight ECG leads to be amplified. Once all the eight ECG lead signals are amplified in the Amplification Cycle, the microcontroller 220 waits for its timer to trigger the next Amplification Cycle.

A buffered attenuator 240 stage at the output of digital-to-analog converter (D/A) 200 is preferably used to map the digital-to-analog converter's full scale output voltage range to the required DC offset cancellation voltage range. As a result, it is possible to get maximum resolution in the digital-to-analog converter voltage steps, for DC subtraction. If the attenuator function is not utilized, then the buffered attenuator 240 stage performs the function of only buffering the output of the digital-to-analog converter 200.

The software low-pass digital filter (LPDF) 190a of each ECG lead, computes and closely tracks the time varying DC offset (i.e. the LPDF tracks the DC drift) present in the digitized ECG lead signal. The DC offset computed for the particular ECG lead in its previous Amplification Cycle is converted to corresponding analog voltage equivalent and subtracted from the signal of the same ECG lead, at the programmable gain amplifier (PGA) 160.

The frequency response of the low-pass digital filters (LPDF) 190*a* can be changed to any desired value by changing the coefficients of the filters in software. For example, for diagnostic-quality ECG, the low-pass digital filters can be configured to have a frequency cut-off at 0.05 Hz, whereas, for monitoring-quality ECG the low-pass digital filters can be configured to have a frequency cut-off at 0.5 Hz. The output of the respective low-pass digital filter is the computed and extracted DC drift, below its programmed cut-off frequency. The output of a low-pass digital filter with a frequency cut-off of 0.5 Hz, tracks the DC drift much faster (and has lesser settling time) as compared to a low-pass digital filter with a frequency cut-off setting of 0.05 Hz. The output of low-pass digital filter (which is the extracted DC drift) of each ECG lead is subtracted from the signal of the same ECG lead in its next amplification cycle and as a result, the DC drift gets eliminated at the output of the PGA amplifier 160.

The resultant effect of extracting the DC time varying DC offset (using a low-pass digital filter) from a signal and subtracting the DC time varying DC offset (i.e. DC drift) from the same signal, is similar to having a hardware high-pass filter (HPF) stage (with the same cut-off frequency as that of the low-pass digital filter) between the differential amplifier 150 and the programmable gain amplifier (PGA) 160. As a result, changing the (higher) cut-off frequency of the low-pass digital filter 190*a* results in a similar change in the (lower) cut-off frequency of the simulated high-pass filter response of the amplifier channel. For example, when the output of a particular ECG lead's low-pass digital filter with a programmed cut-off frequency of 0.5 Hz is subtracted from the signal of the same ECG lead, the amplifier channel exhibits a frequency response similar to a 0.5 Hz high-pass filter in the signal path.

Thus, the amplifier channel can exhibit independent AC (high-pass filter) frequency response for each ECG lead and the AC frequency response can be programmed by programming the frequency response of the corresponding ECG lead's low-pass digital filter 190*a* in software. This technique enables the multiplexed amplifier channel hardware to have a software programmable AC response right up to DC, without increasing the settling time of the amplifier channel.

In order to prevent signal distortion while removing the DC drift, it is necessary to limit the maximum possible gain of the programmable gain amplifier (PGA) 160 by the ratio of resolution of digital-to-analog converter (D/A) 200 to the resolution of analog-to-digital converter (A/D) 180. For example, if the digital-to-analog converter 200 has 16-bit resolution and the required analog-to-digital converter 180 resolution is a 10-bit resolution, then it is necessary to limit the maximum possible gain of the programmable gain amplifier 160 to 64 (i.e. $2^{16}/2^{10}$). It is necessary to limit the gain of the programmable gain amplifier 160 to ensure that the digital-to-analog converter (D/A) 200 remains capable of providing sufficiently small voltage steps for DC subtraction, without distorting the amplified output. It is possible to increase the limit of the maximum permissible gain of the programmable gain amplifier 160 either by increasing the resolution of the digital-to-analog converter 200 or by decreasing the resolution of the analog-to-digital converter 180 or both.

If the programmable gain amplifier (PGA) 160 has a gain higher than unity and the DC offset present in the ECG signal changes abruptly by a large magnitude, the output of low-pass digital filter (LPDF) 190*a* saturates and the low-pass digital filter 190*a* is no longer able to track the DC present in the signal. For example, if the analog-to-digital converter (A/D) 180 and the digital-to-analog converter (D/A) 200 has a full-scale range of 3 volts and the programmable gain amplifier 160 has a gain of 10, the low-pass digital filter 190*a* is able to track abrupt DC offset changes up to $1/10^{th}$ of the 3 volt full scale voltage range (i.e. up to 0.3 volt), after which, the output of the low-pass digital filter saturates. In such a scenario, whenever the output of the low-pass digital filter (LPDF) 190*a* of a particular ECG lead saturates, a Quick Baseline Restoration Algorithm (QBRA) 190*b* (for that particular ECG lead) may be used to bring the low-pass digital filter 190*a* and the programmable gain amplifier (PGA) 160 out of saturation.

The digital output of the low-pass digital filter 190*a* is named LPDF_DC. If the digital output of a particular ECG lead's low-pass digital filter (LPDF) 190*a* goes into saturation, the digital representations of the ECG signal (which are equivalent to the filtered output of the PGA 160) are passed to that particular ECG lead's Quick Baseline Restoration Algorithm (QBRA) 190*b* instead of passing them to the low-pass digital filter (LPDF) 190*a*. Then, the particular ECG lead's Quick Baseline Restoration Algorithm (QBRA) 190*b* is enabled and the low-pass digital filter 190*a* is disabled until the QBRA 190*b* restores the ECG signal's baseline to the required digital baseline value (BASE_VAL). Over several subsequent Amplification Cycles of the particular ECG lead, the Quick Baseline Restoration Algorithm (QBRA) 190*b* checks the digital representations of the particular ECG lead's signal, and depending on whether the signal is in positive or negative saturation, the QBRA 190*b* increments or decrements the digital value to the digital-to-analog converter (D/A) 200, in fixed steps, to consequently increase or decrease the particular ECG lead's Null-Offset voltage. As a result, the Null-Offset voltage quickly approaches the DC offset present in the ECG signal. When the Null-Offset voltage equals the DC offset present in ECG signal, the particular ECG signal's baseline is restored to its required baseline value (BASE_VAL). The digital-to-analog converter's (D/A) 200 digital input value (named as DA_VAL) at which the Null-Offset voltage equals the DC offset present in the signal (i.e. the DA_VAL at which the ECG baseline is restored to its required baseline value) is saved in memory and is named QBRA_DC. Once the particular ECG lead signal is restored to its required digital baseline value (BASE_VAL), the Quick Baseline Restoration Algorithm (QBRA) 190*b* is disabled, the output of the low-pass digital filter (LPDF) 190*a* is re-initialized to the required baseline value (BASE_VAL) and then low-pass digital filter 190*a* is re-enabled for that particular ECG lead. Henceforth (i.e. after baseline restoration), the digital representations of the particular ECG signal are passed through its low-pass digital filter 190*a* and the output of the low-pass digital filter (named as LPDF_DC) starts tracking the DC offset present in the ECG signal. Henceforth, the low-pass digital filter 190*a* can track the DC offset present in the ECG signal over the entire full scale range of the analog-to-digital converter 180, (i.e. 3 volt in the above example) as long as the frequency of DC drift is less than the cut-off frequency of the low-pass digital filter. When the low-pass digital filter is active, the digital value (DA_VAL) to be fed to the digital-to-analog converter (D/A) 200 for generating the Null-Offset is calculated by the following equation:

$$DA\_VAL = QBRA\_DC + (LPDF\_DC - BASE\_VAL) \times K, \text{ where K is a constant.}$$

Assuming that the buffered attenuator 240 does not attenuate the output of the digital-to-analog converter 200 and assuming that the analog-to-digital converter 180 and the digital-to-analog converter 200 have the same full-scale voltage range, the value of K can be calculated by the following equation:

$$K = (D/A \text{ resolution})/(A/D \text{ resolution} \times PGA \text{ gain})$$

The programmable gain amplifier 160 is controlled by the digital input/output (DIO) 210 pins of the microcontroller 220 to provide programmable gain under software control. The amplifier channel can have independent programmable gain for each ECG lead signal, without much increase in the number of hardware components.

The anti-aliasing filters 170 are also configurable through software control, and depending on the application (considering sampling rate per signal and number of signals to be amplified), the anti-aliasing filter can also be configured by the microcontroller (using DIO pins 210) for different frequency cut-offs to match the required bandwidth and reduce high frequency noise. Additionally, anti-aliasing functionality can also be implemented in software by making multiple (typically four) analog-to-digital measurements for each amplified analog sample and averaging the same to compute an averaged digital representation, in order to reduce noise.

Figure 2:
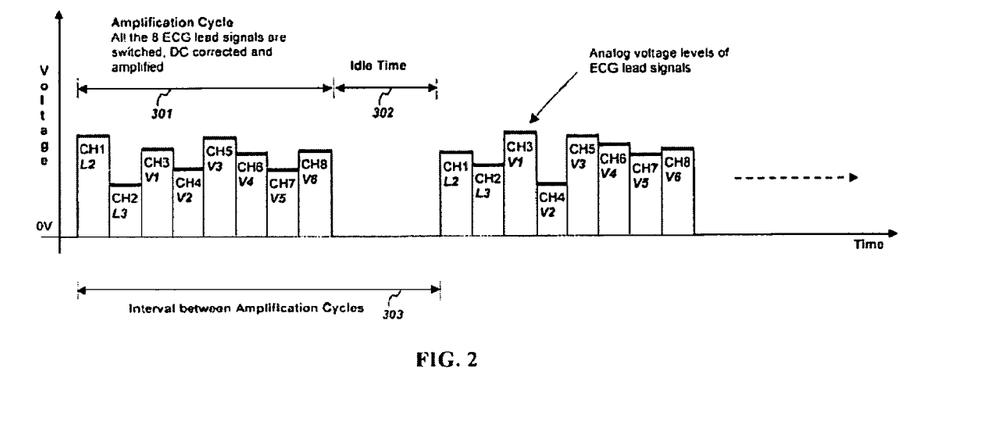
FIG. 2 shows a typical waveform at the output of programmable gain amplifier of FIG. 1, to illustrate the timing of the ECG Amplification Cycles according to an embodiment of the invention.

FIG. 2 shows a typical amplification sequence for amplifying eight ECG leads signals, illustrated by the waveform at the output of the programmable gain amplifier (PGA) 160 according to an embodiment of the invention. Referring to FIG. 2, CH1 through CH8 represent the amplifier channel sequence numbers corresponding to L2, L3 and V1 through V6, which represent the names of the eight ECG lead signals to be amplified. Each ECG Amplification Cycle 301 includes ECG lead selection (i.e. switching), DC-removal and amplification of all eight ECG lead signals, in a sequence. Once all the eight ECG leads are amplified, the amplifier remains idle 302 until the next Amplification Cycle. The ECG lead Amplification Cycle is continuously and periodically repeated at a rate of 500 times a second for diagnostic-quality ECG and at a rate of 200 times a second for monitoring-quality ECG, for example. The Amplification Cycle repeats every 2 milliseconds for diagnostic-quality ECG and every 5 milliseconds for monitoring-quality ECG for the above example. The interval between Amplification Cycles 303 as well as the Amplification Cycle duration 301 is programmable by software.

Figure 3:
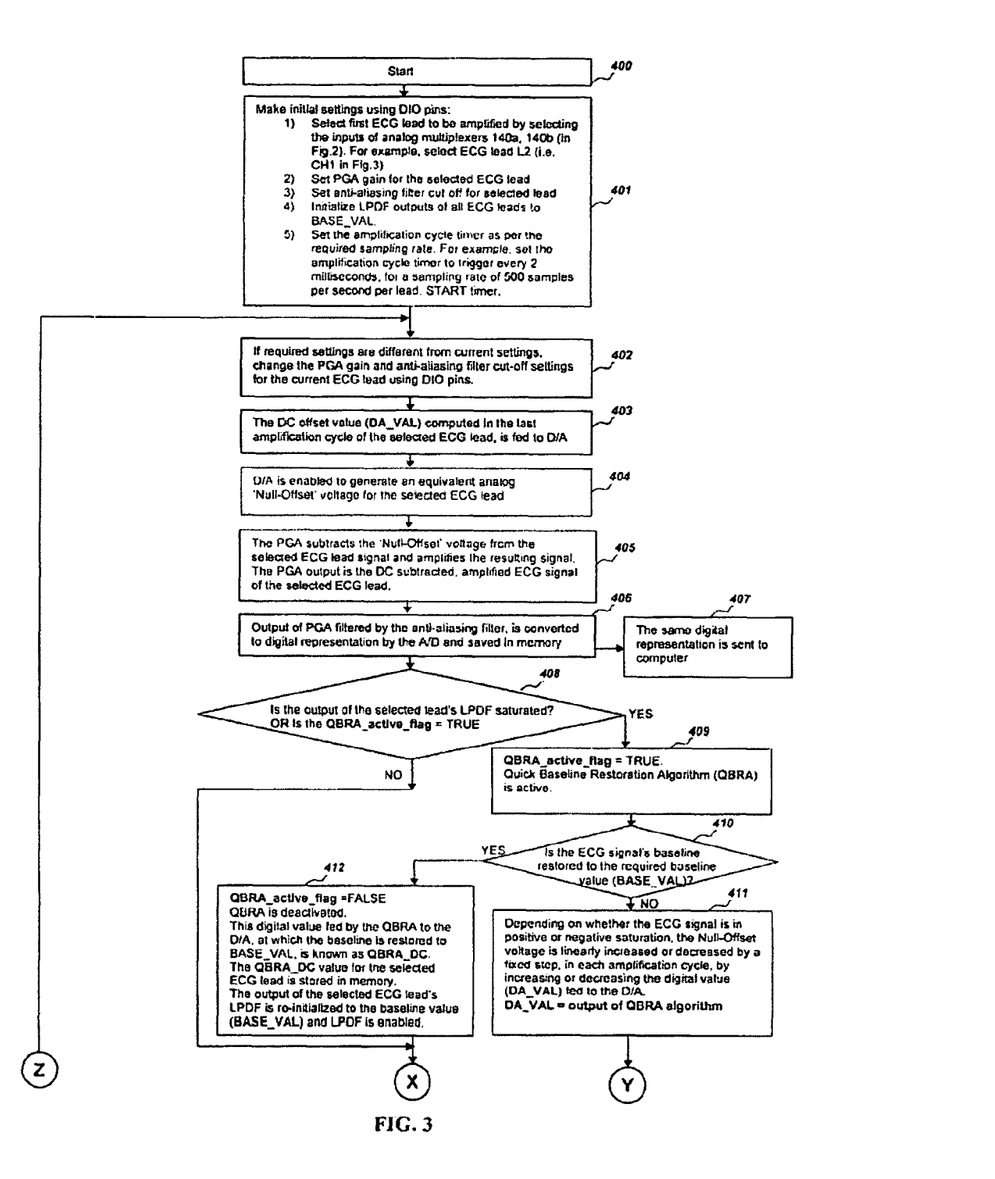
FIG. 3 shows the flow of events in the ECG lead selection, digitization, DC offset subtraction and amplification of ECG lead signals.
Figure 4:
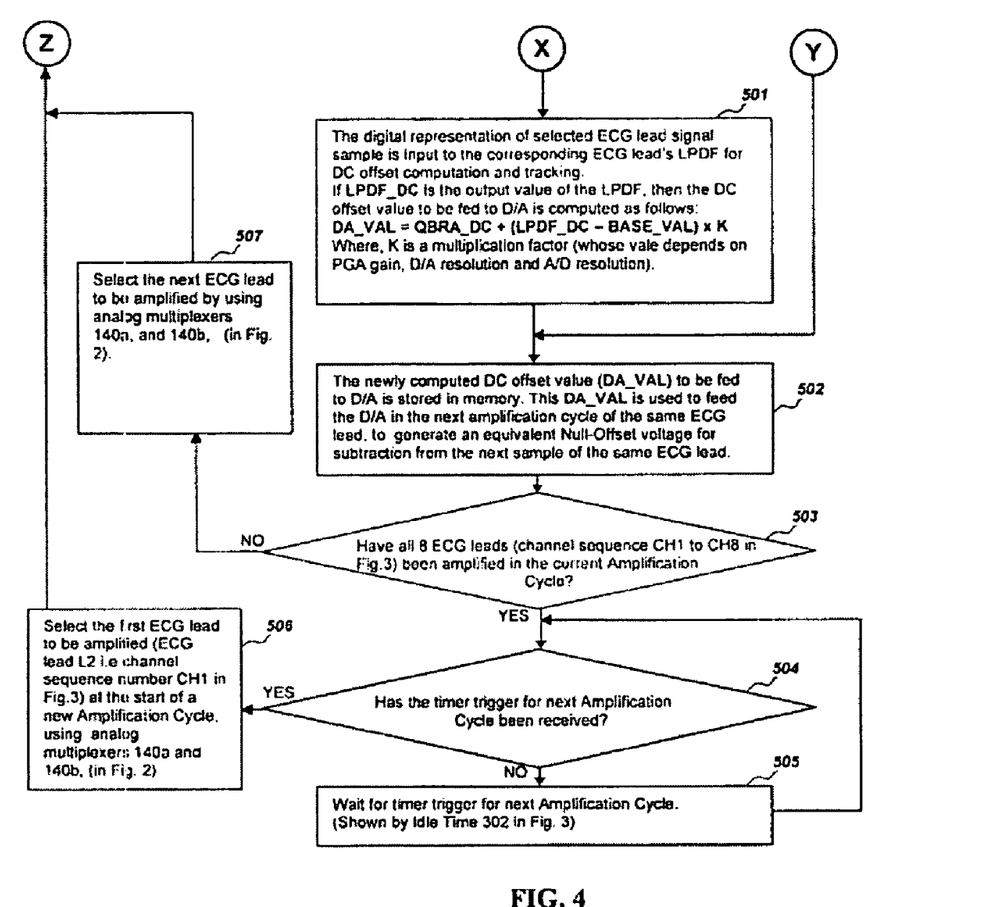
FIG. 4 is a continuation of FIG. 3.
Figure 5:
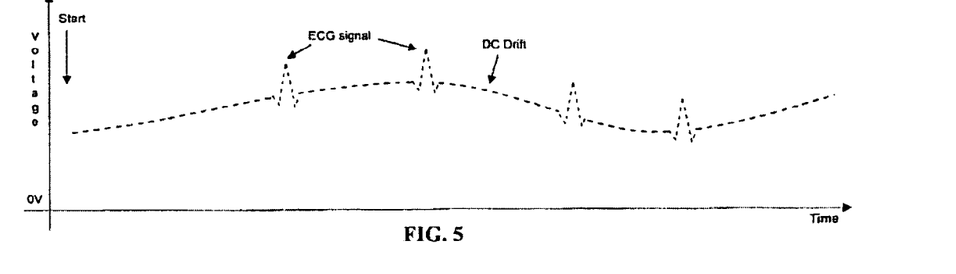
FIG. 5 shows a waveform at the positive input of the programmable gain amplifier of FIG. 1, for a particular ECG lead.

FIG. 3 and FIG. 4 show the flow of events in the ECG lead selection, DC removal, amplification and digitization of ECG lead signals according to an embodiment of the invention. FIG. 4 is a continuation of FIG. 3. Referring to FIG. 3, the process begins at 400 and at 401 the amplifier channel is configured with initial settings, such as the first ECG lead to be amplified, the gain of programmable gain amplifier (PGA) 160 and anti-aliasing filter 170 cut-off frequency settings for the selected ECG lead. Also the outputs of the low-pass digital filters (LPDF) 190a, of all the ECG leads, are initialized to the required baseline value (BASE_VAL) in the software. The microcontroller programs its internal timer to trigger an Amplification Cycle as per the required sampling rate, (for example, every 2 ms for a sampling rate of 500 samples per second per lead for diagnostic-quality ECG) and starts the timer. Then, at 402, the gain of programmable gain amplifier is changed using the digital input/output pins (DIO) 210, if the required gain is different from that of the current setting. Also, the cut-off frequency of the anti-aliasing filter 170 can be changed, if the required setting is different from the current setting. At 403, the digital value of computed DC offset, (i.e. DA_VAL, computed using either the output of low-pass digital filter or the output of Quick Baseline Restoration Algorithm) computed in the last Amplification Cycle of the selected ECG lead, is fed to the digital-to-analog converter (D/A) 200. If the current Amplification Cycle is the first cycle, a DC offset value equal to zero is fed to the D/A 200. Then, at 404, the digital-to-analog converter (D/A) 200 is enabled to generate an equivalent analog voltage, called as the 'Null-Offset' voltage for the selected ECG lead. The 'Null-Offset' voltage is connected to the negative input of the programmable gain amplifier (PGA) 160. At 405, the programmable gain amplifier (PGA) 160 subtracts the 'Null-Offset' voltage from the selected ECG lead signal and amplifies the resultant signal. The programmable gain amplifier's output is a DC-subtracted and amplified ECG signal. Then at 406, the output of the programmable gain amplifier (PGA) 160, filtered by the anti-aliasing filter 170, is digitized by the analog-to-digital converter (A/D) 180 and converted to a digital representation. This digital representation of the DC-corrected and amplified ECG lead signal is saved in memory and also sent to the computer, at 407. The QBRA_active_flag is a software variable which is set to TRUE by the Quick Baseline Restoration Algorithm (QBRA) 190b, as long as the QBRA is active (i.e. until the baseline restoration process is active). At 408, the microcontroller checks whether the output of low-pass digital filter (LPDF) 190a (of the selected ECG lead) is in saturation and also whether the variable QBRA_active_flag set to TRUE. If either of the above conditions is met, the Quick Baseline Restoration Algorithm (QBRA) 190b is activated at 409 and the QBRA_active_flag is set to TRUE. The QBRA 190b remains active until the ECG signal baseline is restored to the required digital baseline value (BASE_VAL). The quick baseline restoration process is done at 409, 410, 411 and 412 and these blocks comprise the Quick Baseline Restoration Algorithm (QBRA) 190b. At 410, the microcontroller checks whether the Selected ECG lead signal has been restored to the required digital baseline value (BASE_VAL). If not, then at 411, the microcontroller either linearly increases or linearly decreases (depending on whether the ECG signal is in positive or negative saturation) the Null-Offset voltage by a fixed step in each Amplification Cycle of the selected ECG lead, by increasing or decreasing the digital value (DA_VAL) fed to the digital-to-analog converter (D/A) 200. As a result, the Null-Offset voltage approaches the DC offset present in the ECG signal after a few Amplification Cycles. Since the Null-Offset is subtracted from the ECG signal at the programmable gain amplifier (PGA) 160 in every Amplification Cycle of the selected ECG lead, the ECG signal gets restored to its required baseline value (BASE_VAL) when the Null-Offset equals the DC offset present in the signal. Once ECG baseline is restored to its required baseline value (BASE_VAL) the condition at 410 returns a 'YES' and then the program, at 412, deactivates the Quick Baseline Restoration Algorithm (QBRA) 190b and sets the QBRA_active_flag to FALSE. Also, at 412, the digital value (DA_VAL) fed to the digital-to-analog converter 200, at which Null-Offset equals the DC offset in the signal, is stored in memory as QBRA_DC. Once the ECG signal baseline is restored to its required digital baseline value (BASE_VAL), the ECG lead's Quick Baseline Restoration Algorithm (QBRA) 190b is disabled, the low-pass digital filter (LPDF) 190a output is re-initialized to the required baseline value (BASE_VAL) and then the low-pass digital filter 190a for the selected ECG lead is re-enabled. Henceforth (after baseline restoration), in the current and the following Amplification Cycles, the digital representations of the selected ECG lead signal are input to its corresponding low-pass digital filter (LPDF) 190a, at 501 in FIG. 5, and the low-pass digital filter's output values (LPDF_DC) start tracking the DC offset present in the ECG signal. Also, at 501, the digital value (DA_VAL), which is to be fed to the digital-to-analog converter (D/A) 200 (for generating the Null-Offset voltage) in the next Amplification Cycle of the same ECG lead, is computed using the output LPDF_DC of the low-pass digital filter using the below equation, as explained earlier:

$$DA\_VAL = QBRA\_DC + (LPDF\_DC - DA\_BASE\_VAL) \times K$$

At 502, this newly computed DC offset value (DA_VAL) to be fed to the digital-to-analog converter (D/A) 200 is stored in memory. This DA_VAL is used as input to feed the digital-to-analog converter (D/A) 200 in the next Amplification Cycle of the same ECG lead, to generate an equivalent Null-Offset voltage for subtraction from the next sample of the same ECG lead. At 503, the microcontroller checks whether the above process is repeated and completed for all the eight ECG leads to be amplified, in the current Amplification Cycle. If amplification and digitization of all the eight ECG leads (through the process mentioned above) is not completed for the current Amplification Cycle, the microcontroller 220, at 507, selects the next ECG lead to be amplified using the analog multiplexers 140*a* and 140*b* as shown in FIG. 1. When the above amplification and digitization process is completed for all eight ECG lead signals, the microcontroller waits, at 504 and 505, until the trigger for the next Amplification Cycle is generated by the system timer (which is configured to trigger every 2 milliseconds in the above example). This waiting interval is shown as 'Idle Time' 302 in FIG. 2. When the trigger for the next Amplification Cycle is received, the microcontroller 220, at 506, selects the first ECG lead to be amplified (i.e. Lead 2 or L2, same as the channel sequence number CH1) in the new Amplification Cycle, by selecting the ECG lead using analog multiplexers 140*a* and 140*b* (shown in FIG. 1) and the program control is again passed to 402. In the new Amplification Cycle all the eight ECG leads are DC-corrected, amplified and digitized as described above and then the microcontroller 220 again waits for the next timer trigger to start a new Amplification Cycle. The Amplification Cycles are repeated continuously at a rate equal to the required sampling rate per ECG lead signal (for example, at a rate of 500 Amplification Cycles per second for diagnostic-quality ECG).

Figure 6:
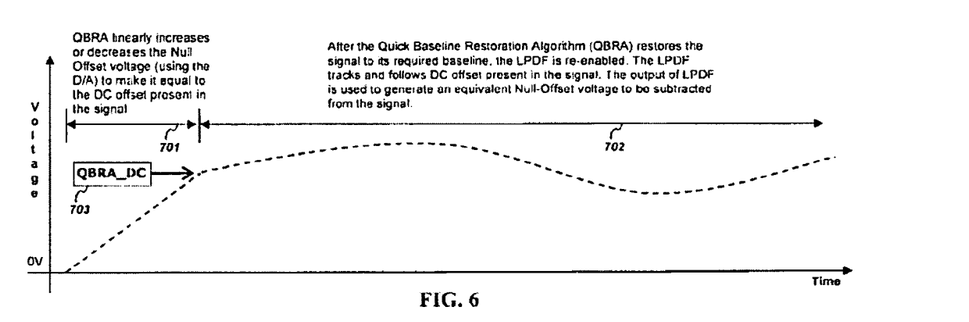
FIG. 6 shows a waveform of the Null-Offset voltage, fed back for subtraction at the negative input of the programmable gain amplifier of FIG. 1, for the same ECG lead as in FIG. 5.
Figure 7:
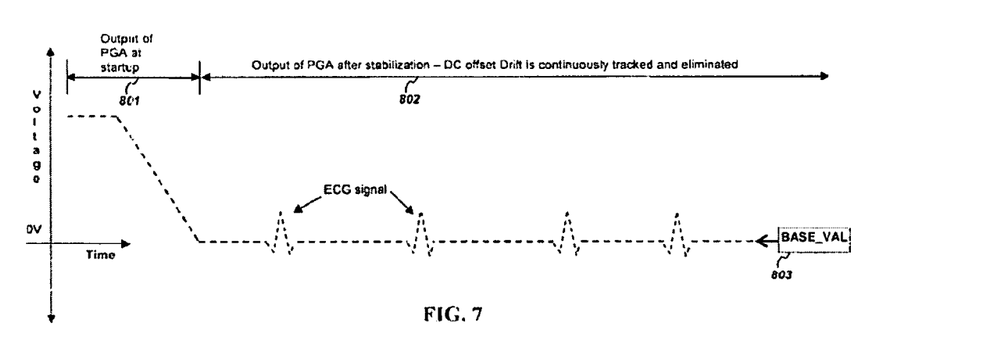
FIG. 7 shows a DC offset subtracted and amplified ECG waveform at the output of the programmable gain amplifier (PGA) 160 of FIG. 1 for the same ECG lead as in FIG. 5.

FIG. 5, FIG. 6 and FIG. 7 show time synchronized typical waveforms at different locations in the multiplexed single amplifier channel, shown for a particular ECG lead.

In particular, FIG. 5 shows a waveform at the positive input of programmable gain amplifier (PGA) 160 for a particular ECG lead. The waveform shows sampled ECG signal on a relatively large and varying DC offset.

FIG. 6 shows a waveform of the Null-Offset voltage, which is fed-back for subtraction at the negative input of programmable gain amplifier (PGA) 160, for the same ECG lead as in FIG. 5. The Null-Offset voltage is generated by feeding the computed DC offset (DA_VAL) to the digital-to-analog converter (D/A) 200. At the start, shown by the time interval 701, the computed DC offset DA_VAL is computed using output of Quick Baseline Restoration Algorithm (QBRA) 190*b*. In the time interval 701, the QBRA 190*b* causes the Null-Offset to quickly and linearly approach the DC offset present in the ECG signal. The digital value of the digital-to-analog converter (D/A) 200 input, at which the Null-Offset equals the DC offset present in the signal is stored in memory as QBRA_DC and is shown by 703. When the Null-Offset voltage equals the DC offset voltage present in the signal at the end of time interval 701, the baseline of the ECG signal gets restored to its required baseline value (BASE_VAL), the Quick Baseline Restoration Algorithm (QBRA) 190*b* for the selected ECG lead is deactivated and the low-pass digital filter (LPDF) 190*a* of the selected ECG channel is activated. The low-pass digital filter (LPDF) 190*a* is active during the time interval shown by 702. After the time interval 701 (i.e. in 702), the output of the low-pass digital filter (LPDF) 190*a* tracks the DC offset present in the ECG signal and the output of LPDF 190*a* is used to compute the DC offset (DA_VAL) to be used as input to the digital-to-analog converter (D/A) 200 for generating the Null-Offset voltage.

FIG. 7 shows the DC drift subtracted ECG waveform at the output of programmable gain amplifier (PGA) 160 for the same ECG lead as in FIG. 5. This waveform results at the output of the programmable gain amplifier 160 when the computed Null-Offset voltage waveform (in FIG. 6) is subtracted from input ECG waveform (in FIG. 5), by the programmable gain amplifier 160. In the time interval 801, the output of the programmable gain amplifier (PGA) 160 is quickly brought out of saturation by the Quick Baseline Restoration Algorithm (QBRA) 190*b*, as the Null-Offset voltage quickly approaches the DC offset present in the input ECG signal and gets subtracted from the input ECG signal at the PGA 160. At the end of time interval 801, when the Null-Offset voltage equals the DC offset in the signal, the ECG signal gets restored to the required digital baseline value BASE_VAL, shown by 803. In time interval 802, the low-pass digital filter (LPDF) 190*a* is activated and used to track and cancel-out the DC drift from the input ECG signal. As seen in 802, DC offset tracked by the low-pass digital filter (LPDF) 190*a* is eliminated from the ECG signal.

As mentioned earlier, the total number of electronic components required to implement a conventional 12-Lead ECG system can be stated as N×C+F. However, according to various embodiments of the invention, the number of electronic components required to implement a 12-Lead ECG multiplexed amplifier can be stated as C+F rather than (N×C)+F. This reduces the form factor, printed circuit board complexity, power consumption and cost.

According to a further embodiment of the invention, amplifier's AC response can be controlled and changed through software. For example, it is possible to set the AC frequency response of the amplifier to 0.05 Hz for diagnostic-quality 12-Lead ECG or to 0.5 Hz for a monitoring-quality ECG, by just changing the low-pass digital filter 190*a* coefficients in software.

According to an embodiment of the invention, it is possible to set individual gains for different ECG lead signals without increasing hardware complexity.

According to a further embodiment of the invention, it is possible to set the number of ECG signals to be amplified through software control. For example, it is possible to configure the multiplexed amplifier channel to amplify eight ECG lead signals for diagnostic ECG or to amplify two ECG lead signals for monitoring ECG and keep the amplifier in idle state for rest of the time, to save power consumption.

According to yet another embodiment of the invention, the frequency response of the anti-aliasing filter 170 can be configured differently for different applications, through software control, without much increase in hardware complexity. This allows this method to be used in a variety of devices, not just an ECG amplifier.

According to an embodiment of the invention, since all signals are passed through the same amplifier channel, all ECG signals get amplified uniformly. Inter-channel gain differences due to component tolerances or due to environmental variations are eliminated. All ECG signals are subjected to the same variations and the same gain factor.

This application discloses several numerical range limitations that support any range within the disclosed numerical ranges even though a precise range limitation is not stated verbatim in the specification because the embodiments of the invention could be practiced throughout the disclosed numerical ranges. Finally, the entire disclosure of the patents and publications referred in this application, if any, are hereby incorporated herein in entirety by reference.

The invention claimed is:

1. An apparatus, comprising:
    two or more multiplexers, wherein lead signals are input to the two or more multiplexers;
    a single amplifier channel, where the outputs of the two or more multiplexers are input to the single amplifier channel; and
    a microcontroller configured to control the two or more multiplexers, wherein the microcontroller stores software which is configured to select, in sequence, one at a time, at least one of the lead signals to be connected to inputs of the single amplifier channel and determine a direct current (DC) offset value of each of the lead signals to be applied to the lead signals in the single amplifier channel based on the lead signals in a previous amplification cycle, wherein the single amplifier channel amplifies the lead signals.

2. The apparatus of claim 1, wherein the single amplifier channel comprises a differential amplifier, a programmable gain amplifier and an anti-aliasing filter.

3. The apparatus of claim 2, wherein the microcontroller comprises an analog-to-digital converter and a digital-to-analog converter.

4. The apparatus of claim 2, wherein
    a selected lead signal is connected to an input of the differential amplifier;
    an output of the differential amplifier is fed to an input of the programmable gain amplifier for DC offset removal and further amplifications;
    an output of the programmable gain amplifier is adapted to be filtered by the anti-aliasing filter;
    the output of the anti-aliasing filter is adapted to be digitized by the microcontroller using an analog-to-digital converter; and
    the microcontroller is capable of selecting the next lead signal to be amplified by using the multiplexers.

5. The apparatus of claim 4, wherein the microcontroller comprises hardware or software which is adapted to simulate a high-pass filter to remove DC offset by computing the DC offset from a voltage signal from the digitized outputs of the anti-aliasing filter, converting the DC offset to an analog representation by the digital-to-analog converter, and subtracting the DC offset back from the same lead signal in a next amplification cycle.

6. The apparatus of claim 5, wherein the software comprises code to model low-pass filter stages for the lead signals.

7. The apparatus of claim 6, wherein the low-pass filter is adapted to compute and track the time varying DC offset present in the digitized outputs of the anti-aliasing filter.

8. The apparatus of claim 6, further comprising a baseline restoration algorithm that is adapted to bring the low-pass digital filter and the programmable gain amplifier out of saturation.

9. The apparatus of claim 6, wherein frequency responses of the low-pass filters is adjustable to a desired value by changing coefficients of the filters in the software, wherein AC frequency response of the amplifier channel is programmable in the software.

10. The apparatus of claim 2, wherein a maximum gain of the programmable gain amplifier is capable of being limited by a ratio of resolution of a digital-to-analog converter to a resolution of an analog-to-digital converter to prevent signal distortion while removing the DC offset.

11. The apparatus of claim 1, wherein an alternating current(AC) response of the single channel amplifier is capable of being controlled and changed through software.

12. The apparatus of claim 2, wherein the anti-aliasing filter is configured by the microcontroller for different frequency cut-offs to match a required bandwidth and to reduce high frequency noise.

13. An apparatus, comprising:
    two or more multiplexers, wherein lead signals are adapted to be input to the two or more multiplexers;
    at least one amplifier channel, where the outputs of the two or more multiplexers are capable of being input to the at least one amplifier channel and wherein the number of amplifier channels is less than a number of lead signals; and
    a microcontroller which is adapted to control the two or more multiplexers, the microcontroller comprising hardware or software which is configured to simulate a high-pass filter to remove DC offset by computing the DC offset and subtracting the DC offset back from the same lead signal in a next amplification cycle, wherein the at least one amplifier channel is capable of amplifying the lead signals.

* * * * *